United States Patent

Brink et al.

Patent Number: 6,054,400
Date of Patent: Apr. 25, 2000

[54] BIOACTIVE GLASSES AND THEIR USE

[76] Inventors: Maria Brink, Stampvägen 4 E 133, FIN-20540Åbo; Kaj Karlsson, Dragonvägen 48, FIN-20720Åbo; Antti Yli-Urpo, Värttinägatan 17, FIN-20660 Littoinen, all of Finland

[21] Appl. No.: 08/860,200

[22] PCT Filed: Jan. 2, 1996

[86] PCT No.: PCT/FI96/00001

§ 371 Date: Jul. 11, 1997

§ 102(e) Date: Jul. 11, 1997

[87] PCT Pub. No.: WO96/21628

PCT Pub. Date: Jul. 18, 1996

[30] Foreign Application Priority Data

Jan. 13, 1995 [FI] Finland .................................. 950147

[51] Int. Cl.$^7$ .................................................. C03C 3/097
[52] U.S. Cl. ................................ 501/63; 501/70; 501/7; 106/35; 433/212.1; 433/228.1; 633/16
[58] Field of Search ................................ 501/63, 70, 72; 106/35; 623/16; 433/212.1, 228.1

[56] References Cited

U.S. PATENT DOCUMENTS

| | | | |
|---|---|---|---|
| 5,429,996 | 7/1995 | Kaneko | 106/35 |
| 5,432,130 | 7/1995 | Rheinberger et al. | 501/63 |
| 5,648,301 | 7/1997 | Ducheyne et al. | 501/63 |
| 5,713,994 | 2/1998 | Kramer et al. | 501/72 |
| 5,721,049 | 2/1998 | Marolongo et al. | 501/63 |
| 5,735,942 | 4/1998 | Litkowski et al. | 501/63 |

FOREIGN PATENT DOCUMENTS

| | | |
|---|---|---|
| 61-141660 | 6/1986 | Japan . |
| 1477899 | 6/1977 | United Kingdom . |
| 91/12032 | 8/1991 | WIPO . |

*Primary Examiner*—Karl Group
*Attorney, Agent, or Firm*—Kubovcik & Kubovcik

[57] ABSTRACT

The invention relates to a bioactive glass having a suitable working range for glass processing. Said bioactive glass comprises oxides of silicon, phosphorus, alkalis, alkaline earths and optionally other elements such as boron. According to the invention said oxides are present in the following amounts: $SiO_2$ 53–60 wt. %; $Na_2O$ 0–34 wt. %; $K_2O$ 1–20 wt. %; $MgO$ 0–5 wt. %; $CaO$ 5–25 wt. %; $B_2O_3$ 0–4 wt. %; $P_2O_5$ 0.5–6 wt. %; provided that $Na_2O+K_2O=16-35$ wt. %; $K_2O+MgO=5-20$ wt. % and $MgO+CaO=10-25$ wt. %.

15 Claims, 8 Drawing Sheets

BIOACTIVE GLASSES AND THEIR USE

FIELD OF THE INVENTION

This invention relates to novel bioactive glasses with a large working range and controlled durability. Furthermore, the invention relates to the use of said bioactive glasses for tissue bonding purposes in the medical or dental field; for use in biotechnology; for controlled release of agents and for tissue guiding.

BACKGROUND OF THE INVENTION

The publications and other materials used herein to illuminate the background of the invention, and in particular, cases to provide additional details respecting the practice, are incorporated by reference.

In recent years intensive studies have been made on artificial materials called biomaterials to be introduced in the human body for repairing damages therein. The body conditions offer a severe environment for these materials. The combination of increased temperatures, salt solutions, destructive enzymes, organic acids capable of forming different complexes, proteins and dissolved oxygen in the body provides a most corrosive environment. The body is also extremely sensitive to foreign materials and easily shows signs of poisoning, rejecting reactions and allergic responses.

Only a very limited number of materials is accepted in soft or hard tissue as a substrate. These materials can e.g. be used as artificial implants supporting crowns and fixed bridges in dentistry, and in maintenance and augmentation of alveolar ridges (1). They may also be used as fillings in bone defects and in periodontal pockets, as capping materials in endodontics, and in orthopaedic, plastic, ear, nose and throat surgery (2). The materials can be used as granules and bulk materials to fill bone cavities and defects, and as coatings and bulk materials for artificial joints. The oral implants are in continuous contact with both hard and soft tissues, and the implant material should therefore develop an intime contact with both hard and soft tissue.

Biomaterials are defined as non-living materials that are used in the human body, and which are intended to interact with different biological systems. These materials can be either inert, resorbable or bioactive (1).

Inert biomaterials, e.g. carbon, some ceramics, metals, alloys and certain polymers, do not cause any measurable reaction in the body. The carbons include, for example, pyrolytic carbon, glassy carbon, carbon fibers and composites and they are used as heart valve stents and in orthopaedic surgery (1). Examples of inert ceramics are $Al_2O_3$ and $ZrO_2$. Metals and alloys used as biomaterials are e.g. stainless steel, titanium, tantalum and certain alloys. These metals and alloys are not surface active, i.e. a chemical bond does not develop between the material and the body tissue. Their durability is difficult to control in the body, and they are mainly used in orthopaedic and maxillofacial surgery (1).

Resorbable biomaterials are typically organic polymers, e.g. PGA (polyglycolic acid) and PLA (polylactic acid) which gradually degrade in the body and disappear (1).

Bioactive materials are surface active materials able to chemically bond to body tissue. This group includes bioactive glasses, glass ceramics and ceramics. The bioactive glass is amorphous. Bioactive glass ceramics are materials having crystalline particles embedded in the amorphous glass phase. Bioactive ceramics have a crystalline structure. When the bond between the bioactive material and the body tissue is a successful one, a layer of silica rich gel is found at the surface of the glass. The bone-bonding occurs when the build-up of bone-like apatite on top of this silica gel occurs (5,7,8,9). These bioactive materials are used as bulk materials, granules and coatings.

Ceramics as biomaterials can be either inert, resorbable or bioactive (1). Bioactive ceramics are e.g. calcium phosphates and aluminium calcium phosphates and they are used in orthopaedic surgery and as dental implants. The most common problems with these materials relate to crystallization. The crystalline structure makes them difficult to work and it is troublesome to control the crystallization. The wear and degradation mechanisms as well as durability of the ceramics are not very well understood.

Bioactive glass ceramics are composites comprising crystals embedded in an amorphous glassy phase. Glass ceramics contain different crystalline phases in controlled amounts in the material. These phases are mainly controlled by heat-treatment. Ceravital® is a trademark for a glass ceramic developed in Germany and it contains a glassy phase and an apatite one. Cerabone® A-W is a trademark for glass ceramics developed in Japan. This material contains phases of apatite, wollastonite and glass (9).

Bioactive glasses have been in use for about 20 years as bone filling materials and prostheses in odontology, orthopaedy and opthalmology. Some of the existing bioactive glasses can bond to both soft and hard tissue (4, 5, 8, 9). The use of bioactive glasses is, however, restricted since they are brittle. To overcome the disadvantages due to the brittle properties, the glasses can be reinforced by making glass ceramics. Another possibility would be to use the glass as coatings on metal substrates. In this way, both the mechanical properties of the metal and the special bone-bonding property of the glass could be obtained. In prostheses prepared in this way the metal could take the mechanical load while the glass enables the prostheses to be anchored to the surrounding tissue. The thermal expansion of the glass must, however, match that of the metal, and the solubility of the glass must be low enough to provide the bond for several years (3). The existing bioactive glasses do not possess an acceptable viscosity-temperature dependence and therefore bioactive glasses described hereto are not suitable e.g. as coatings.

The bioactive glasses could, however, find a much larger field of use if glass fibre tissues, spherical granules and coated metal prostheses were available. In odontology, such glass fibre tissues could be used as reinforcements in cheek bone, and coated metal prosthesis could be used by orthopaedics to ensure a good fit in e.g. hip surgery.

Known bioactive glasses have attained a certain clinical use as bone filling materials. They tend, however, to devitrify (crystallize) and their working range is narrow. They can therefore not be used with satisfying results as e.g. coatings on metal prostheses or as glass fibre products. They cannot be manufactured using conventional methods because the curve describing their viscosity-temperature dependence is too steep for most glass forming machines. The main drawbacks relating to the existing bioactive glasses thus derive from their tendency to crystallize. Although the glasses are vitrous materials, some of them crystallize at low temperatures (about 600° C.). This makes them difficult e.g. to sinter into a product or to use for the manufacturing of spherical granules. They are often also phase-separated due to their low content of silica, and the glass composition is therefore different from batch to batch. They have a narrow working range. FIG. 1 shows log η as function of temperature (η is expressed in dpa·s) for a bioactive glass of type 2-92 (number 39 in Table 1 below) which represents a glass with a narrow working range. The glass crystallizes as indicated by the steep part of the viscosity curve above 1000° C. The narrow working range makes it impossible or extremely difficult to produce glass fibres and other fibre products, as well as to cast into various moulds. The reaction in tissue is rapid, which in some cases may cause too strong a reaction in the body. Thus the only remaining product that can be made from these glasses is granules.

SUMMARY OF THE INVENTION

The object of this invention is to provide bioactive glasses that chemically bond to hard and soft tissue. Further requirements are that said bioactive glasses provide a rapid healing process, are capable of maintaining the bone structure, and have a controlled short- or long-term durability. The bioactive glasses shall further have the required mechanical properties and be resorbable when wished. In addition, said bioactive glasses must be easy to manufacture and form and therefore they must have a large working range. The glasses must not devitrify and their sterilization should not give rise to problems.

It has now surprisingly been found that bioactive glasses fulfilling the above requirements are obtained by adding potassium and optionally also magnesium to the glass forming composition. By doing so, a suitable viscosity-temperature dependence is obtained, and the glass does not devitrify. The bioactivity is, however, retained.

The invention thus concerns novel bioactive glasses having a suitable working range for glass processing said glasses comprising oxides of silicon, phosphorus, alkalis, alkaline earths and optionally other elements such as boron wherein said oxides are present in the following amounts:

| | |
|---|---|
| $SiO_2$ | 53–60 wt-% |
| $Na_2O$ | 0–34 wt-% |
| $K_2O$ | 1–20 wt-% |
| MgO | 0–5 wt-% |
| CaO | 5–25 wt-% |
| $B_2O_3$ | 0–4 wt-% |
| $P_2O_5$ | 0.5–6 wt-% | provided that

| | |
|---|---|
| $Na_2O + K_2O =$ | 16–35 wt-% |
| $K_2O + MgO =$ | 5–20 wt-%, and |
| $MgO + CaO =$ | 10–25 wt-%. |

Preferably, the amount of the components varies within the following ranges:

| | |
|---|---|
| $SiO_2$ | 53–56 wt-% |
| $Na_2O + K_2O$ | 18–30 wt-% |
| $K_2O + MgO$ | 7–20 wt-% |
| $MgO + CaO$ | 12–25 wt-% | the remaining components being as defined before.

A particularly large working range is obtained if the glass composition contains $P_2O_5$ 1–4 wt-% and $B_2O_3$ 1–4 wt-%.

Bioactive glasses with a large working range have a particularly high durability in the following composition range:

| | |
|---|---|
| $SiO_2$ | 53–60 wt-% |
| $Na_2O$ | 0–19 wt-% |
| $K_2O$ | 1–17 wt-% |
| MgO | 3–5 wt-% |
| CaO | 5–22 wt-% |
| $B_2O_3$ | 0–4 wt-% |
| $P_2O_5$ | 0.5–6 wt-% | provided that

| | |
|---|---|
| $Na_2O + K_2O =$ | 16–20 wt-% |
| $K_2O + MgO =$ | 5–20 wt-%, and |
| $MgO + CaO =$ | 10–25 wt-%. |

Especially good results are obtained with $SiO_2$ 54–56 wt-%.

Bioactive glasses with large working range have a particularly low durability in the following composition range:

| | |
|---|---|
| $SiO_2$ | 53–56 wt-% |
| $Na_2O$ | 5–33 wt-% |
| $K_2O$ | 2–20 wt-% |
| MgO | 0–3 wt-% |
| CaO | 7–25 wt-% |
| $B_2O_3$ | 0–2 wt-% |
| $P_2O_5$ | 2–6 wt-% | provided that

| | |
|---|---|
| $Na_2O + K_2O =$ | 25–35 wt-% |
| $K_2O + MgO =$ | 5–20 wt-%, and |
| $MgO + CaO =$ | 10–25 wt-%. |

A particularly preferable bioactive glass is characterized by the following composition: $SiO_2$ 54 wt-%; $Na_2O$ 12 wt-%; $K_2O$ 15 wt-%; MgO 5 wt-%; $P_2O_5$ 2 wt-%; CaO 11 wt-% and $B_2O_3$ 1 wt-%.

Another particularly preferable bioactive glass is characterized by the composition consisting of $SiO_2$ 53 wt-%; $Na_2O$ 6 wt-%; $K_2$ 12 wt-%; MgO 5 wt-%; $P_2O_5$ 4 wt-% and CaO 20 wt-%.

Furthermore the invention concerns the use of the novel bioactive glasses with a large working range and controlled durability in the medical or dental field as bulk materials (dense or porous), as coatings, as crushed or spherical granules, as glass wool and other fibre products (single fibres, tissues, cords, fabrics) or as a combination of such products.

The invention concerns also composites of said novel bioactive glasses with alloys, metals, polymers, hydroxyapatite and other glasses.

The invention concerns further the use of said bioactive glasses in biotechnology as absorbents or adsorbents for phosphorus or calcium from a surrounding medium.

BRIEF DESCRIPTION OF THE DRAWINGS

FIG. 3 represents glass type 17-93 (No. 23 in Table 1); FIG. 4 represents glass type 5-92 (No. 21 in Table 1) and FIG. 5 represents glass type 1-92 (No. 18 in Table 1).

DETAILED DESCRIPTION OF THE INVENTION

The bioactive glasses according to this invention have a large working range and a controlled durability. The controlled durability enables the production of bioactive glasses with a slow initial reaction in hard and soft tissue, and this slow reaction causes minimal irritating reactions when the glass is implanted. Although the glasses possess a high bioactivity their resorption rate can be predicted and controlled. Some of these glasses are very slowly resorbable but are still bioactive. These properties enable a use in younger patients, and also to implant large quantities of the material into sensitive tissue and blood. High durability in combination with bioactivity makes the use as thin coatings, and thin glass fibres and fibre tissues possible. Thin plates as well as small spherical granules and granule agglomerates may also be used.

Advantages with Glasses with a Large Working Range

Figure 1:
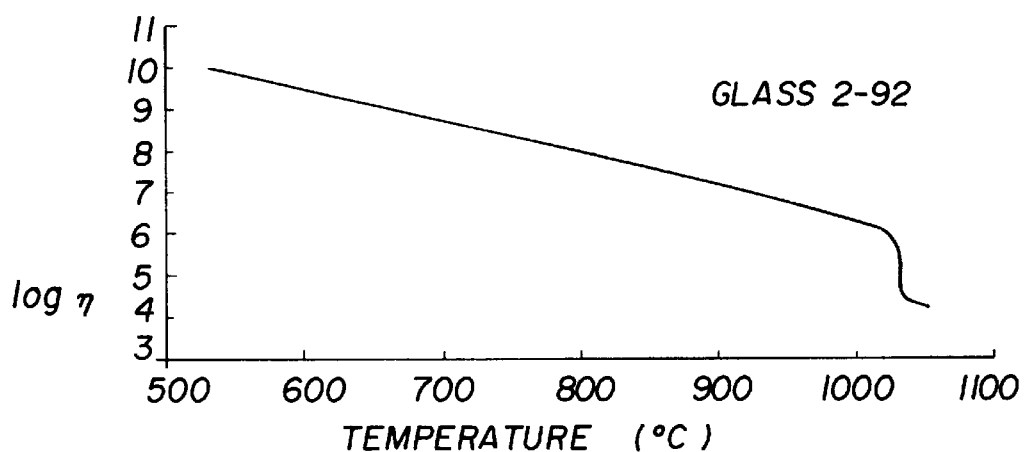
FIG. 1 shows the viscosity-temperature dependence for a bioactive glass (type 2-92, number 39 in Table 1) having such a narrow working range that it crystallizes during the measurements.
Figure 2:
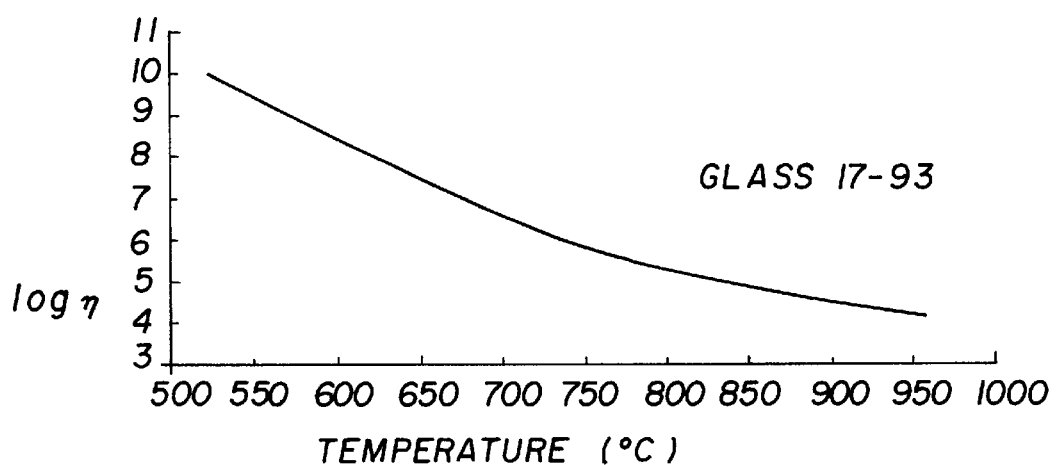
FIG. 2 shows the viscosity-temperature dependence for a bioactive glass (type 17-93, number 23 in Table 1) having a large working range.

Bioactive glasses with a large working range make casting an easy process, and it is also possible to manufacture fibres and different fibre products. The production of spherical granules is possible too, because these glasses are not phase-separated, and these granules can then be sintered without crystallization. FIG. 2 shows the viscosity-temperature dependence for a bioactive glass with a large working range, i.e. glass type 17-93 (number 23 in Table 1 below; η expressed in dPa·s). The flat shape of the curve indicates that said glass possesses a large working range. The large working range enables the glass to be blown into different shapes, and the coating process onto different materials is possible. The glass can be handled outside the furnace without risk for crystallization. Non-bioactive glasses with a large working range are well known, but bioactive glasses with a large working range have not been disclosed prior to the present invention.

Advantages with Glasses with Controlled Durability

The durability of the glasses is possible to control by changes of the shape, the glass composition (as described above) and in the handling of the material, e.g. by heat- and surface treatment. One example is the manufacturing of spherical granules with a surface that is more durable than the inner part. The durability can be affected by heat treatment e.g. by sintering together individual particles to give agglomerates having a specific area less than that of the sum of the individual particles. Another example of affecting the durability by heat treatment is the choise of appropriate annealing temperature and rate. The durability can further be influenced by surface treatment e.g. by etching, by chemical or physical surface modification, and by ion exchange etc. By these means, the reactivity during processing, manufacturing, sterilisation and storage is possible to control both in tissue and in vitro.

Experiments

Investigations of 40 different glasses in the system $Na_2O$—$K_2O$—$MgO$—$CaO$—$B_2O_3$—$P_2O_5$—$SiO_2$ have been made. The composition of the glasses is disclosed in Table 1. Out of these 40 glasses certain glass compositions were selected for further studies both in vitro and in vivo. The amount of the individual components in the glasses selected for the studies varied in the ranges shown in Table 2. The viscosity and corrosion behaviour in vitro for the glasses have been examined according to known methods (6). The investigations in vivo were made in hard tissue in rabbits, and in soft tissue in rats. The durability was determined according to a standard method. The protein adsorption properties were investigated using a fast plasma protein adsorption test. The workability of the glasses was tested by manufacturing spherical granules, fibres and blown cylinders.

TABLE 1

Composition of the investigated glasses in the seven-component system consisting of oxides of Na, K, Mg, Ca, B, P and Si in wt %.

| No. | Glass | $Na_2O$ | $K_2O$ | MgO | CaO | $B_2O_3$ | $P_2O_5$ | $SiO_2$ |
|---|---|---|---|---|---|---|---|---|
| 1 | 7-92 | 10 | 5 | 0 | 15 | 0 | 0 | 70 |
| 2 | 18-92 | 15 | 0 | 2 | 15 | 0 | 0 | 68 |
| 3 | 13-92 | 0 | 15 | 5 | 10 | 0 | 3 | 67 |
| 4 | 4-92 | 10 | 5 | 2 | 10 | 0 | 6 | 67 |
| 5 | 10-92 | 10 | 5 | 0 | 15 | 3 | 3 | 64 |
| 6 | 8-92 | 15 | 0 | 5 | 10 | 0 | 6 | 64 |
| 7 | 16-92 | 5 | 10 | 2 | 20 | 0 | 0 | 63 |
| 8 | 23-93 | 3 | 12 | 5 | 14 | 1 | 2 | 63 |
| 9 | 11-93 | 6 | 9 | 0 | 17 | 2 | 6 | 60 |
| 10 | 25-93 | 12 | 3 | 2 | 17 | 3 | 4 | 59 |
| 11 | B7-94 | 21 | 6 | 0 | 10 | 0 | 4 | 59 |
| 12 | 19-92 | 5 | 10 | 2 | 15 | 3 | 6 | 59 |
| 13 | 6-92 | 10 | 5 | 5 | 15 | 3 | 3 | 59 |
| 14 | 15-93 | 9 | 9 | 2 | 20 | 2 | 0 | 58 |
| 15 | B6-94 | 19 | 7 | 1 | 11 | 0 | 4 | 58 |
| 16 | 24-93 | 9 | 6 | 2 | 17 | 3 | 6 | 57 |
| 17 | B5-94 | 19 | 6 | 1 | 13 | 0 | 4 | 57 |
| 18 | 1-92 | 15 | 0 | 5 | 20 | 3 | 0 | 57 |
| 19 | B4-94 | 17 | 7 | 2 | 13 | 1 | 4 | 56 |
| 20 | 22-93 | 21 | 9 | 2 | 8 | 1 | 4 | 55 |
| 21 | 5-92 | 20 | 10 | 5 | 10 | 0 | 0 | 55 |
| 22 | B3-94 | 17 | 6 | 2 | 15 | 1 | 4 | 55 |
| 23 | 17-93 | 18 | 9 | 0 | 14 | 1 | 4 | 54 |
| 24 | B2-94 | 15 | 7 | 3 | 15 | 2 | 4 | 54 |
| 25 | 12-93 | 12 | 3 | 5 | 20 | 0 | 6 | 54 |
| 26 | 9-93 | 12 | 15 | 5 | 11 | 1 | 2 | 54 |
| 27 | 13-93 | 6 | 12 | 5 | 20 | 0 | 4 | 53 |
| 28 | B1-94 | 15 | 6 | 3 | 17 | 2 | 4 | 53 |
| 29 | 14-93 | 18 | 6 | 2 | 17 | 2 | 2 | 53 |
| 30 | 18-93 | 18 | 6 | 2 | 20 | 1 | 0 | 53 |
| 31 | 19-93 | 15 | 12 | 2 | 11 | 3 | 4 | 53 |
| 32 | 21-93 | 15 | 15 | 0 | 14 | 1 | 2 | 53 |
| 33 | 17-92 | 20 | 10 | 2 | 10 | 3 | 3 | 52 |
| 34 | 12-92 | 20 | 10 | 5 | 10 | 3 | 0 | 52 |
| 35 | 3-92 | 25 | 5 | 2 | 10 | 3 | 3 | 52 |
| 36 | 20-92 | 15 | 15 | 2 | 15 | 3 | 0 | 50 |
| 37 | 14-92 | 20 | 10 | 5 | 20 | 0 | 3 | 42 |
| 38 | 11-92 | 25 | 5 | 2 | 20 | 0 | 6 | 42 |
| 39 | 2-92 | 20 | 10 | 5 | 20 | 0 | 6 | 39 |
| 40 | 15-92 | 15 | 15 | 2 | 20 | 3 | 6 | 39 |

The glasses were prepared by melting the raw materials at 1300–1600° C. In the experiments the raw materials $Na_2CO_3$, $K_2CO_3$, MgO, $CaCO_3$, $H_3BO_3$ and $CaHPO_4 2H_2O$ were of analytical grade. $SiO_2$ was added as sand. Alternatively, commercial raw materials could have been used. The glasses can be used as quenched and re-melted to improve the homogeneity in the glass. When the glass is intended for medical use it may be melted in a Pt/Au crucible to avoid contamination. Potassium and optionally magnesium are used to affect the physical properties so as to give glasses with a large working range.

The coatings as well as the manufacturing of different fibre products are performed by known methods. The manufacturing of spherical granules may be performed by flame-spraying. Some of the glasses are not phase-separated or sensitive to devitrify, and this enables a repeated heat-treatment do be done, if necessary.

Particularly preferable bioactive glasses with a large working range and controllable durability were found in compositions where the $SiO_2$ content was about 53–54 wt-%. However, the range within the attractive glasses are expected to be found is estimated to about 53–60 wt-% of $SiO_2$.

Testing Methods and Results

In all, forty glasses within the composition range described in Table 2 were tested.

TABLE 2

The composition range for the glasses studied

| Component | Range |
| --- | --- |
| $Na_2O + K_2O$ | 15–30 wt-% |
| $K_2O$ | 0–15 wt-% |
| $MgO + CaO$ | 10–25 wt-% |
| $MgO$ | 0–5 wt-% |
| $B_2O_3$ | 0–3 wt-% |
| $P_2O_5$ | 0–6 wt-% |
| $SiO_2$ | 39–70 wt-% |

The durability was determined according to a standard method and the viscosity-temperature dependence was measured in a high-temperature microscope. Reactions in hard tissue were established and three glasses were implanted into soft tissue. The results were compared to those achieved when the glass was soaked in a simulated body fluid (SBF) (7). The protein adsorption properties for eleven glasses was also determined. The workability was tested by manufacturing spherical granules of a bioactive glass by flame-spraying. One bioactive glass was also chosen for manufacturing blown glass cylinders and fibres of two bioactive glasses were manufactured in a laboratory scale.

Durability

The durability of forty glasses was determined using the Swedish Standard method SS 13 63 21. According to this method, 2 g of glass (particle diameter 300–500 $\mu$m) is kept in 50 ml water at 98±0.5° C. for one hour. Twenty-five millilitres of the solution is neutralised and the result is expressed as amount in millilitre of 0.01 M HCl consumed per gram of glass ($P_{98}$). The results are presented in Table 3.

TABLE 3

Durability ($P_{98}$) for glasses given in milliliters of 0.01M HCl consumed per gram of glass. The glass numbers refer to those given in Table 1.

| No. | $P_{98}$ (ml) | No. | $P_{98}$ (ml) | No. | $P_{98}$ (ml) | No. | $P_{98}$ (ml) |
| --- | --- | --- | --- | --- | --- | --- | --- |
| 1 | 2.15 | 11 | 23.32 | 21 | 19.91 | 31 | 7.80 |
| 2 | 2.95 | 12 | 1.84 | 22 | 4.39 | 32 | 18.10 |
| 3 | 1.56 | 13 | 2.35 | 23 | 9.65 | 33 | 16.71 |
| 4 | 1.45 | 14 | 3.58 | 24 | 3.64 | 34 | 13.18 |
| 5 | 2.51 | 15 | 11.69 | 25 | 2.60 | 35 | 18.48 |
| 6 | 2.01 | 16 | 2.44 | 26 | 6.09 | 36 | 10.07 |
| 7 | 2.99 | 17 | 7.38 | 27 | 2.85 | 37 | 10.53 |
| 8 | 2.24 | 18 | 4.05 | 28 | 3.59 | 38 | 13.79 |
| 9 | 1.95 | 19 | 5.14 | 29 | 4.45 | 39 | 11.86 |
| 10 | 2.81 | 20 | 31.98 | 30 | 4.68 | 40 | 8.61 |

For the applications described below all glasses consuming more than 2.5 ml 0.01 M HCl per gram of glass are of special interest.

Corrosion in a simulated body fluid (in vitro test for bioactivity)

Forty glasses were tested by soaking in a simulated body fluid (SBF) (7). The composition of the solution is given in Table 4. Tests were performed where all glasses were kept for 72 hours, and further some glasses for 24 hours and for 7, 14, 28, 90 and 180 days, respectively, at about 37° C. in SBF at a surface area to solution volume ratio (SA/V)= 0.1–0.4 $cm^{-1}$.

TABLE 4

Ion concentrations (in mM) in the simulated body fluid (SBF, ref. 7). The solution is buffered at pH 7.25 with 50 mM Tris-buffer (($CH_2OH)_3CNH_2$) and 45 mM HCl.

| $Na^+$ | $K^+$ | $Ca^{2+}$ | $Mg^{2+}$ | $Cl^-$ | $HCO_3^-$ | $HPO_4^{2-}$ | $SO_4^{2-}$ |
| --- | --- | --- | --- | --- | --- | --- | --- |
| 142.0 | 5.0 | 2.5 | 1.5 | 147.8 | 4.2 | 1.0 | 0.5 |

The samples were examined by scanning electron microscopy (SEM) and energy dispersive X-ray analysis (EDXA). The surface reactions after corrosion for 72 hours in SBF are presented in Table 5. The glass surface reactions were classified according to the behaviour in SBF into either of four groups, denoted A (inert glasses), B (silica gel), C (sporadic Ca,P) and D (silica gel and Ca,P layer). Low silica and high alkali content in the glass seemed to promote the formation of silica gel and a subsequent precipitation of apatite at the glass surface. Each result in Table 5 is the average of three experiments.

TABLE 5

Surface reactions observed after 72 hours in simulated body fluid (SBF). A = no surface changes (inert); B = silica gel formed; C = sporadic formation of Ca,P and D = silica gel and Ca,P formed. The glass numbers refer to those of Table 1.

| No. | Reaction | No. | Reaction | No. | Reaction | No. | Reaction |
| --- | --- | --- | --- | --- | --- | --- | --- |
| 1 | A | 11 | B | 21 | D | 31 | D |
| 2 | A | 12 | A | 22 | A | 32 | C,D |
| 3 | A | 13 | A | 23 | D | 33 | D |
| 4 | A | 14 | B | 24 | C | 34 | B |
| 5 | A | 15 | B | 25 | C,D | 35 | D |
| 6 | A | 16 | C,D | 26 | C | 36 | B |
| 7 | A | 17 | B | 27 | D | 37 | D |
| 8 | A | 18 | C | 28 | C | 38 | D |
| 9 | A | 19 | A | 29 | D | 39 | D |
| 10 | C,D | 20 | C,D | 30 | C | 40 | D |

Viscosity

The viscosity-temperature dependence for forty glasses was determined using a Leitz high-temperature microscope (10). In this microscope, the deformation of a glass cylinder is observed during heating, and the deformation can then be related to the viscosity of the glass melt. The viscosity-temperature dependence was thus measured using a method described in reference (10). The sintering point (SP, log $\eta \approx 10.0$ ($\eta$ is expressed in dPa·s)), the minimum base line point (MBL, log $\eta \approx 6.1$), the half-cone point (HCP, log $\eta \approx 4.55$) and the floating point (FP, log $\eta \approx 4.2$) were used as reference points. The results are presented in Table 6. The reproducibility of the temperature reading was usually ±20° C. The heating of the furnace was max. 12° C./min. Glasses showing a non-Newtonian behaviour as well as signs of crystallization were excluded from the modelling of the results.

Over a large temperature range the viscosity of silica glass obeys quite accurately the equation $$\log \eta = A + B/T$$

where $\eta$ is the viscosity in dpa·s, A and B are constants, and T is the temperature in Kelvin. In the above equation, log $\eta$ is a linear function of 1/T, and the composition dependence of the constants A and B can be estimated using linear regression analysis. The following result was obtained:

$$A = -7.7 + 7.5 \cdot \left(\frac{CaO}{SiO_2}\right) - 9.2 \cdot \left(\frac{B_2O_3}{SiO_2}\right) - 2.5 \cdot \left(\frac{P_2O_5}{SiO_2}\right)$$

$$B = 17048.4 - 5319.2 \cdot \left(\frac{Na_2O}{SiO_2}\right) - 2909.3 \cdot \left(\frac{K_2O}{SiO_2}\right) - 6977.1 \cdot \left(\frac{CaO}{SiO_2}\right)$$

In the equations above, the glass components are given in wt-% and the temperature (T) in Kelvin. The model was tested with a significance level of 95%, the regression coefficient is 92.54% and the estimated residual standard deviation 0.63 dpa·s. All results from the measurements with the high-temperature microscope for glasses containing more than 52 wt-% $SiO_2$ were used in the modelling. The validity range for the model is given in Table 2. The content of $SiO_2$ should, however, for the purpose of the model, be above 52 wt-%.

Reactions in Hard Tissue

Cones (length 4–6 mm, cross section 4–5 mm) of twenty-six glasses selected from the compositions disclosed in Table 1 were implanted into adult New Zealand rabbits for eight weeks. Conical holes were drilled into each tibia using a dental drill irrigated with sterile saline solution. The operations were made under general anaesthesia and standard aseptic conditions. After the rabbits were killed, tissue reactions were studied by light microscopy. The contact between bone and implant in the cortical area was measured histomorphometrically. The remaining part of the tissue was examined by SEM and EDXA to evaluate the reactions in the interface between glass and bone.

Figure 3:
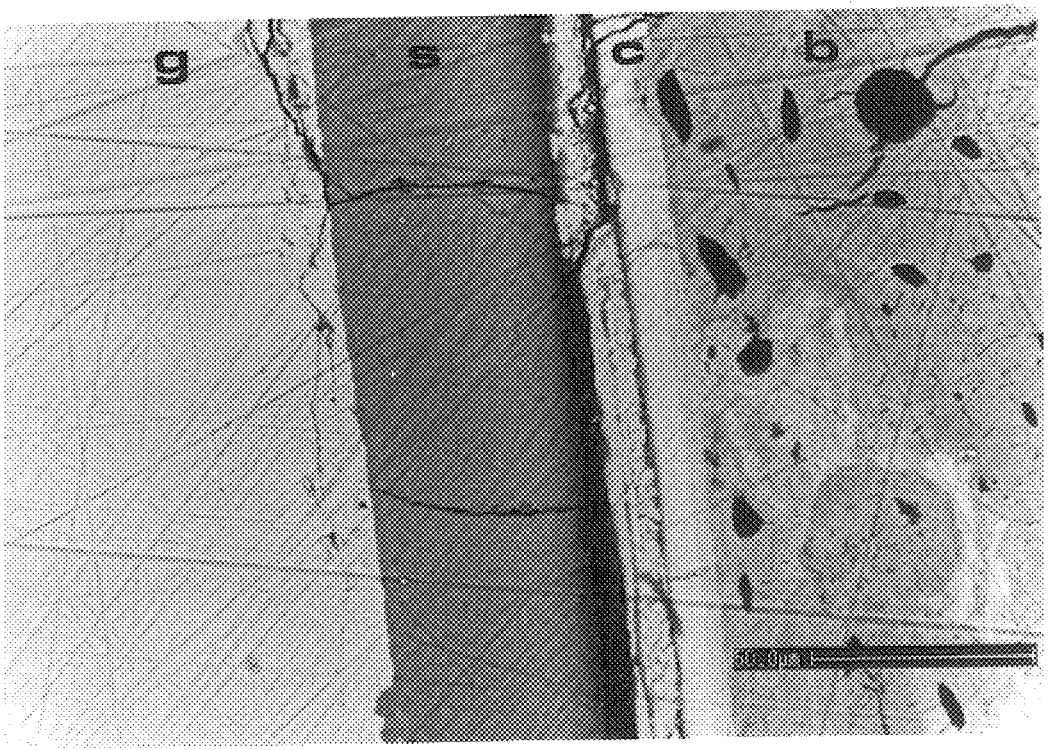
FIGS. 3, 4 and 5 illustrate the contact between bone (b) and glass (g) after eight weeks in rabbit tibia.
Figure 4:
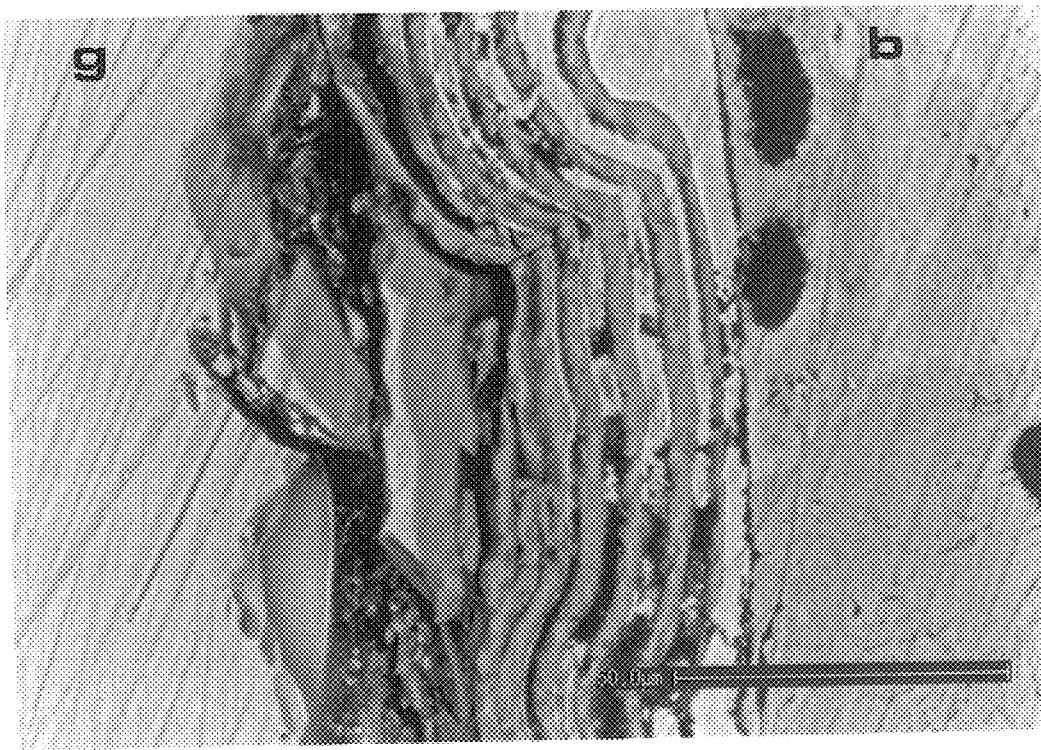
Figure 5:
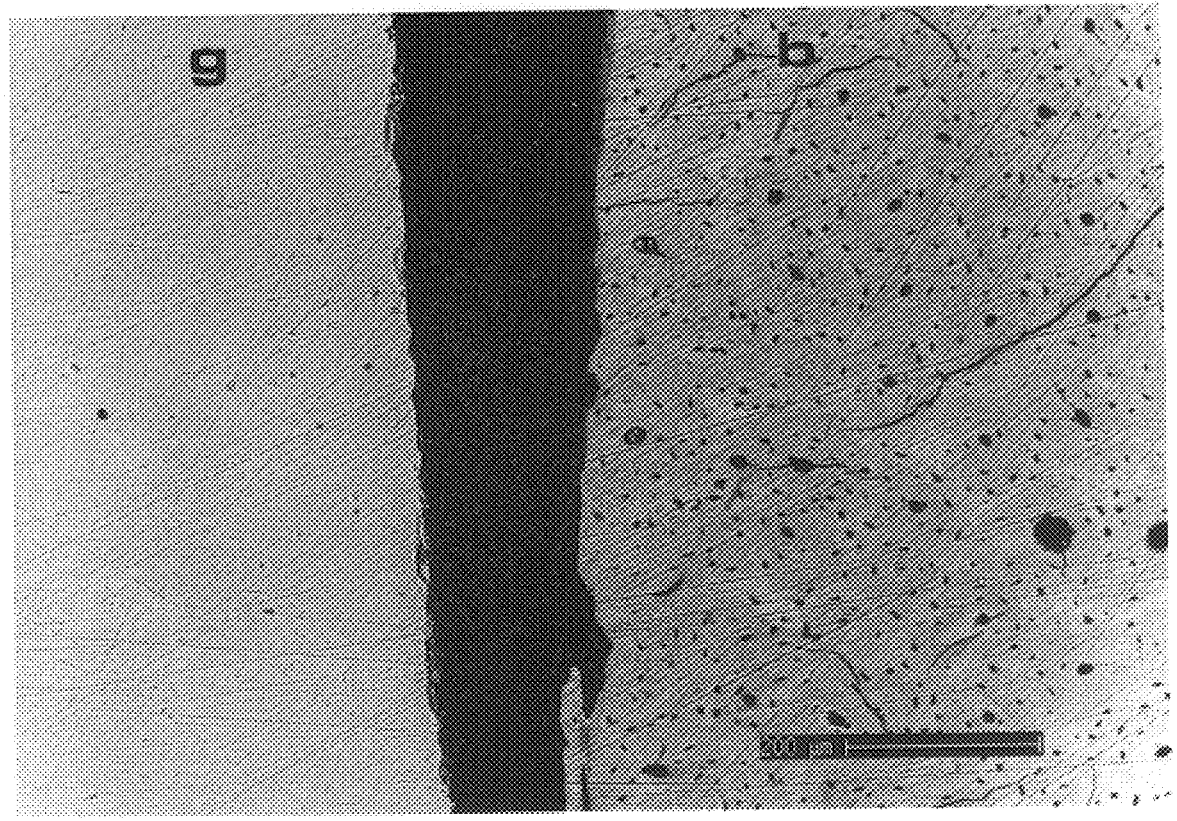

The results are presented in Table 7 and FIGS. 3 to 5. In the Figures "b" designates bone and "g" glass. The build-up of a layer of silica gel and of calcium and phosphate (Ca,P) in the reaction zone between glass and bone was taken as a sign of bioactivity. The reactivity was divided into four groups (A to D) using similar criteria as for the in vitro results. The values for bioactivity, presented in Table 7, are the average result of four or five samples of the same glass. FIG. 3 to 5 illustrate the contact between bone and glass after eight weeks in rabbit tibia. FIG. 3 represents glass type 17-93 (No. 23 in Tables 1 and 7). Layers of silica gel (s) and Ca,P (c) have been built up between the glass (g) and bone (b). FIG. 3 shows that the glass 17-93 is bioactive. FIG. 4 represents glass type 5-92 (No. 21 in Tables 1 and 7). Crusted layers of silica gel (dark stripes) and Ca,P (light stripes) can be seen between the glass (g) and bone (b). FIG. 4 shows that the glass 5-92 possesses a certain degree of bioactivity. FIG. 5 represents glass type 1-92 (No. 18 in Tables 1 and 7). FIG. 5 verifies that this glass type is inert with respect to bioactivity. No layers of silica gel or Ca,P are formed between glass and bone. This glass does not contain $P_2O_5$.

TABLE 6

Average temperature (in ° C.) of two runs in the high-temperature microscope for SP (sintering point), MBL (minimum base line point), HCP (half-cone point) and FP (floating point) for various glasses. The glass numbers refer to those of Table 1.

| No. | SP (° C.) | MBL (° C.) | HCP (° C.) | FP (° C.) | No. | SP (° C.) | MBL (° C.) | HCP (° C.) | FP (° C.) |
|---|---|---|---|---|---|---|---|---|---|
| 1 | 685 | 865 | 1065 | 1145 | 21 | 540 | 850 | 945 | 1000 |
| 2 | 640 | 860 | 1055 | 1100 | 22 | 575 | 755 | 1005 | 1055 |
| 3 | 760* | 975* | 1095* | 1170* | 23 | 535 | 745 | 910 | 970 |
| 4 | 610 | 860 | 1070 | 1160 | 24 | 550 | 780 | 990 | 1010 |
| 5 | 595* | 825* | 955* | 1060* | 25 | 630 | 755 | 1065 | 1090 |
| 6 | 655 | 885 | 1010 | 1115 | 26 | 560 | 715 | 880 | 990 |
| 7 | 615* | 890* | 1135* | 1160* | 27 | 555 | 840 | 1080 | 1105 |
| 8 | 675 | 890 | 1035 | 1155 | 28 | 575 | 795* | 1025* | 1050* |
| 9 | 680 | 880 | 1005 | 1110 | 29 | 555* | 890* | 950* | 985* |
| 10 | 625 | 795 | 935 | 1040 | 30 | 570 | 1040 | 1120 | 1125 |
| 11 | 565° | 780 | 900 | 955° | 31 | 550 | 720 | 865 | 965 |
| 12 | 590 | 905 | 1040 | 1185 | 32 | 550 | 795 | 915 | 985 |
| 13 | 595 | 785 | 870 | 1005 | 33 | 525 | 790 | 930 | 955 |
| 14 | 625 | 775 | 1070 | 1095 | 34 | 520 | 875 | 950 | 995 |
| 15 | 595° | 790 | 920 | 1025° | 35 | 525 | 875 | 920 | 930 |
| 16 | 630 | 846 | 985 | 1090 | 36 | 535 | 875 | 975 | 1010 |
| 17 | 565 | 760 | 975 | 1010 | 37 | 530 | 975 | 990 | 1005 |
| 18 | 605 | 760 | 1065 | 1085 | 38 | 530 | 1010 | 1085 | 1095 |
| 19 | 560 | 755 | 975 | 1020 | 39 | 545 | 990 | 1010 | 1030 |
| 20 | 525 | 735 | 855 | 950 | 40 | 530 | 955 | 995 | 1010 |

*Average of three measurements.
°Result from one measurement.

TABLE 7

Glass reactions after eight weeks in rabbit tibia. A = no reaction (inert); B = silica gel formation observed; C = layered structure of silica gel and Ca,P observed and D = silica gel and Ca,P observed (good bioactivity). The numbers refer to those of Table 1.

| No. | Re-action | No. | Reaction | No. | Reaction | No. | Reaction |
|---|---|---|---|---|---|---|---|
| 1 | A | 11 | — | 21 | B,C | 31 | C,D |
| 2 | A | 12 | A | 22 | — | 32 | — |
| 3 | A | 13 | A | 23 | D | 33 | D |
| 4 | A | 14 | A | 24 | — | 34 | C |
| 5 | A | 15 | — | 25 | — | 35 | D |
| 6 | A | 16 | — | 26 | C,D | 36 | C |
| 7 | A | 17 | — | 27 | D | 37 | D |
| 8 | — | 18 | A | 28 | — | 38 | D |
| 9 | — | 19 | — | 29 | C,D | 39 | D |
| 10 | — | 20 | — | 30 | B | 40 | D |

Glasses denoted bioactive in the in vivo test, group D, caused no or very mild mononuclear inflammatory reaction in bone marrow. Inflammation in the other bioactivity groups A-C varied from mild to moderate. Small clusters of giant cells were observed in connection with a few glass cones of all bioactivity groups. In group D, a delicate fibrous capsule surrounded the tip of the glass cone projecting to the medullar space. This capsule tended to be thicker around the tips of the glass cones with lower in vivo surface reactions.

Some glasses in vivo developed silica gel and Ca,P as a layered structure in the reaction zone between glass and bone. This phenomenon can be seen in FIG. 4, and it was for some glasses with 50–55 wt-% $SiO_2$ and 0–2 wt-% $P_2O_5$. The corresponding reaction in vitro showed sporadic formation of Ca,P on top of silica gel.

The dependence between the glass composition and glass reaction (GR) in vivo can be described as $$GR = -3.90 + 0.18 \cdot Na_2O + 0.20 \cdot K_2O + 0.11 \cdot CaO + 0.48 \cdot P_2O_5 - 3.20 \cdot \frac{(P_2O_5)^2}{SiO_2}$$

with the glass components given in wt-% and with a tested significance level of 95%. The regression coefficient is 88.50% and the estimated residual standard deviation is 0.51. For the purpose of this model, the glass reactions have been expressed numerically so that value A in Table 7 corresponds to a glass reaction=1, B to glass reaction=2, C to 3 and D to 4. The limits for the components in this equation are given in Table 2.

In this experiment, bioactive glasses were found when the silica content was less than 56 wt-%. The probability of finding bioactive glasses depends on the content of alkali, alkaline earths and $P_2O_5$ as well, as seen in the equation above. Glasses, that are especially interesting for the applications described below, are those with less than 61 wt-% $SiO_2$.

Reactions in Soft Tissue

Three bioactive glasses with a large working range and with different durability were implanted subcutaneously in rats. The glasses were 9-93, 13-93 and 17-93. Glass 89-9 (4, 5) was used as reference. A total of 80 adult Long-Evans rats (weight 200–400 g) were used as experimental animals. The surgical procedures were performed under Hypnorm/Dormicum anesthesia. A transcutaneous incision was made at the dorsal area and a subcutaneous space created for the implants. Three glass rods (diameter 0.8–1.2 mm, length 5 mm) were implanted into each rat. The implantation times were 3, 7, 14 and 28 days, and 6 months. After the implantation times, the rats were killed with $CO_2$. The implants were removed with surrounding tissue. The samples were fixed in alcohol and embedded into plastic. The samples were prepared for analysis with light microscopy, SEM and EDXA.

The glasses started to resorb within one week after implantation. The glass reactions after implantation are presented in Table 8.

TABLE 8

Glass reactions after implantation into rat soft tissue. Most of the samples consist of three glass rods. The glass compositions are given in Table 1.

| | Reaction for | | |
|---|---|---|---|
| Time | glass 9-93 | glass 13-93 | glass 17-93 |
| 3 days | Sporadic resorption of the surface (2 samples). | Sporadic resorption of the glass. Layers of silica (Si) and calcium phosphate (Ca.P) (4 samples). | No resorption (2 samples). |
| 7 days | Sporadic resorption of the surface (2 samples). | Resorption of the surface. Layers of Si and Ca.P (4 samples). | Sporadic resorption of the surface (2 samples). |
| 14 days | Resorption of the surface (2 samples). | Resorption of the surface. Layers of Si and Ca.P (3 samples) | Sporadic resorption of the surface (1 sample). |
| 28 days | Resorption of the surface (1 sample). | Resorption of the surface. Layers of Si and Ca.P (4 samples). | Resorption of the surface (2 samples). |
| 6 months | The rods are resorbed to about 70% (3 samples). | The rods are resorbed to about 50%. Layers of Si and Ca.P (1 sample). | The rods are resorbed to about 50%. Layers of Si and Ca.P (4 samples). |

Protein Adsorption

The adsorption of proteins to eleven bioactive glasses (Table 9) has been investigated using a fast plasma protein adsorption test. The results from the protein adsorption tests are compared to those for hydroxyapatite (HA) and an inert glass. The protein profiles were obtained using a plasma protein adsorption test. Albumin was the main protein adsorbed to all bioactive glasses. The protein adsorption properties of the bioactive glasses differed considerably from those of hydroxyapatite and the inert glass.

Human plasma was prepared from blood collected in heparinized tubes. The plasma was separated by centrifuging at 4000×g for 10 minutes, and stored at −20° C. Before use, the plasma was diluted 1:4 in TBS (10 mM Tris-HCl, 150 mM NaCl, pH=7.4). HA, with a grain size of approximately 200 µm, was obtained from BDH Chemicals Ltd, Poole, England and the inert glass from Hackman-iittala, Finland. The inert glass were crushed and sieved (315–500 µm).

Glass particles (100 mg) and HA (50 mg) were incubated with 1 mL of diluted plasma in Nunc CryoTubes (Nunc, Roskilde, Denmark) for 30 minutes by rotation end-over-end at room temperature. After this treatment, the particles were washed with 2 ml of TBS by rolling end-over-end for 1 minute. The adsorbed proteins were analysed with sodium dodecyl sulphate polyacrylamide gel electroforesis (SDS-PAGE, PhastSystem®, Pharmacia, Sweden). The particles were heated at 100° C. for 5 minutes in 120 µl distilled water and 30 µl denaturating buffer (0.2 M Na-phosphate, pH=7.0, containing 15% SDS and 5% glycerol). The cleared solutions were subjected to SDS-PAGE, and stained with silver according to the manufacturer's instructions. The protein standard was obtained from BioRad (Richmond, Calif., USA).

Figure 10:
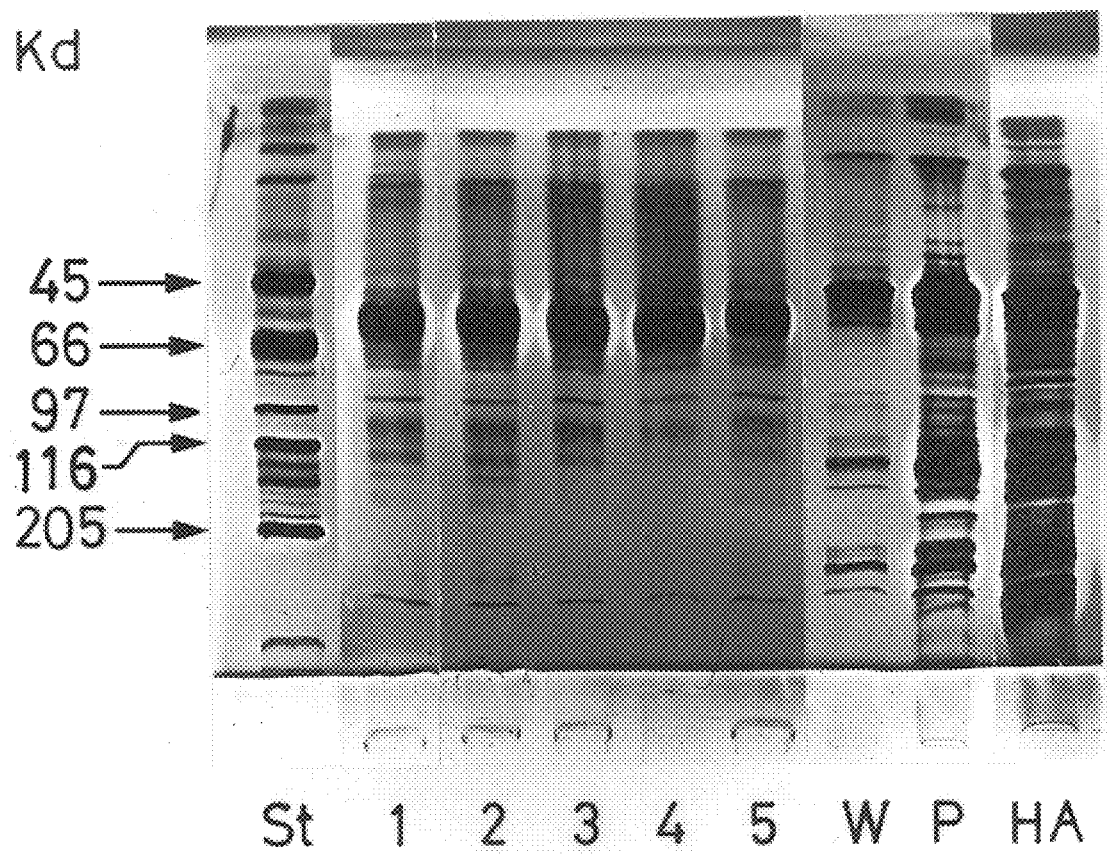
FIG. 10 shows protein adsorption pattern for some bioactive glasses.

All bioactive glasses adsorbed mainly albumin from the plasma. FIG. 10 shows the protein adsorption pattern for some bioactive glasses. The molecular weights in kilodalton (kD) are indicated to the left. Abbreviations: St=standard, 1=glass 9-93, 2=glass 13-93, 3=glass 14-93, 4=glass 17-93, 5=glass 19-13, W=inert, P=plasma and HA=hydroxyapatite. The inert glass showed a broad plasma protein adsorption profile. In addition to albumin, it adsorbed proteins from the molecular weight (MW) range of immunoglobulins (MW~150 kD) and fibrinogen (MW~400 kD). HA showed also a broad plasma protein adsorption profile.

Some differences in the protein adsorption properties were observed between the bioactive glasses. These differences occured especially in the MW-range of immunoglobulins and for proteins with a lower MW than that of albumin (MW~69 kD).

TABLE 9

Glasses used in the protein adsorption test. The compositions are given in Table 1

| | |
|---|---|
| 5-92 | 9-93 |
| 11-92 | 13-93 |
| 12-92 | 14-93 |
| 14-92 | 17-93 |
| 15-92 | 19-93 |
| 20-92 | |

Use of the Bioactive Glasses According to this Invention

The bioactive glass according to the present invention may be used as crushed or spherical granules, dense or porous bulk materials, coatings, glass fibre products, composites and as combinations of the same. The use of the different materials is described below.

Crushed or Spherical Granules

Crushed granules, spherical granules, sintered spherical granules and sintered spherical granules as agglomerates may be used as filling materials in bone defects and in soft tissue, and especially as fillings in periodontal bone pockets, and as dental root fillings and in pulp ectomy. Sintered granules may be suitable for slow release of agents, and can be doped with agents and chemicals. The granules may have a surface that is more durable than the inner part, and the material may, when sintered, be shaped during the surgical operations. The granules may also be implanted by injection. The surface reactivity can be changed by different methods, e.g. by etching and coating.

Figure 6:
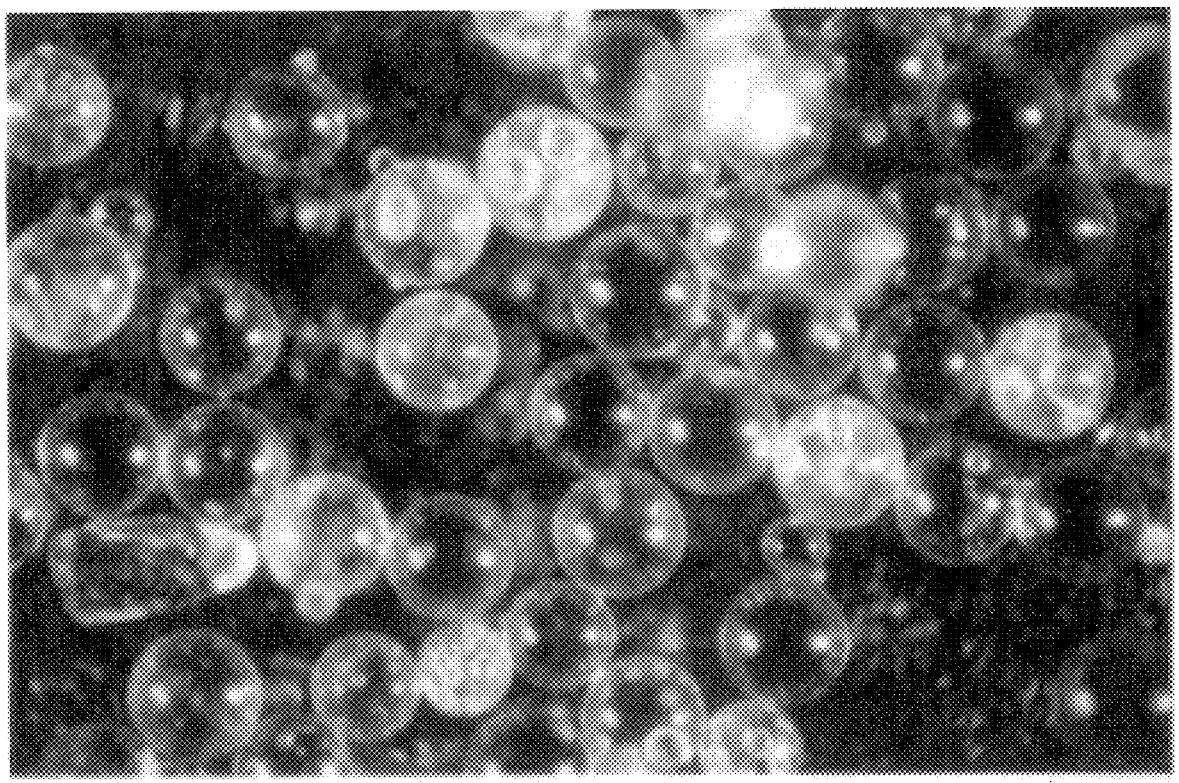
FIG. 6 shows spherical granules made of the bioactive glass 13-93 (No. 27 in Table 1), magnification 250×.

FIG. 6 represents a photograph of spherical granules made of the bioactive glass 13-93 (No. 27 in Table 1), magnification 250×. The granule size is 74–125 µm.

Dense Bulk Materials

Dense bulk materials can be used as crushed or spherical granules described above, i.e. as filling materials in bone defects and in soft tissue, for slow release of agents, and for tissue guiding. The material can be used when manufactured as cast, pressed and blown.

Porous Bulk Materials

Porous bulk materials can be used as crushed or spherical granules and dense bulk materials described above. These products have a defined porosity.

Coatings

The glasses may be used as coatings on e.g. alloys, metals, other glasses and ceramics. The coatings may be of different thicknesses, and the layers can consist of mono- and multilayer coatings. Such coated materials are suitable for use as medical and dental implants (e.g. for hip joints, bone augmentation, equipments and fixation pins and screws) and as biotechnological, dental and medical devices. The coatings can be either dense or porous.

Glass Fibre Products

Glass fibres and wool can be used in the form of single fibres, tissues, fabrics, cords, rings, pressed, tablets and pellets. These materials may be used for the same purposes as crushed or spherical granules, dense bulk materials, porous bulk materials and coatings described above.

Combinations of the Materials

Combinations of the materials described above can be used for the same purposes as the plain materials. As examples can be mentioned spherical granules or fibres used as sintered on coatings, on bulk materials or on granules for controlled durability.

Composites

Composites comprising one or more of the materials described above and alloys, metals, polymers and other glasses can be prepared. Composites of hydroxyapatite in different forms together with these materials can be used as agglomerates, pellets, porous bulk materials, granules or coatings.

Figure 7B:
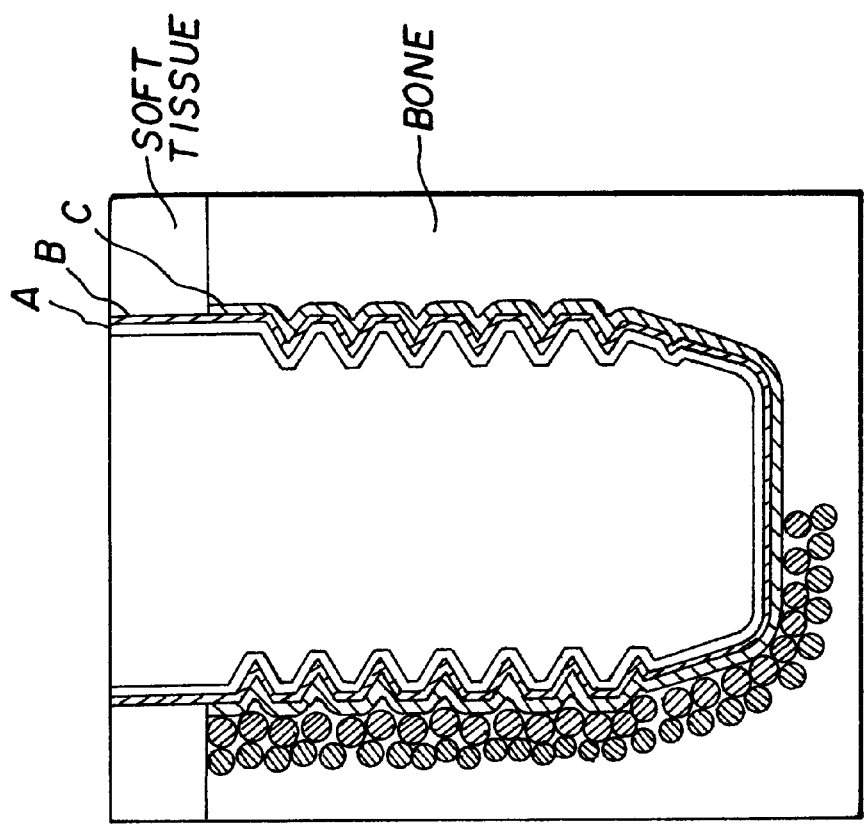
FIGS. 7a and 7b illustrate coatings on a substrate with smooth (FIG. 7a) or rough (FIG. 7b) surface.
Figure 7A:
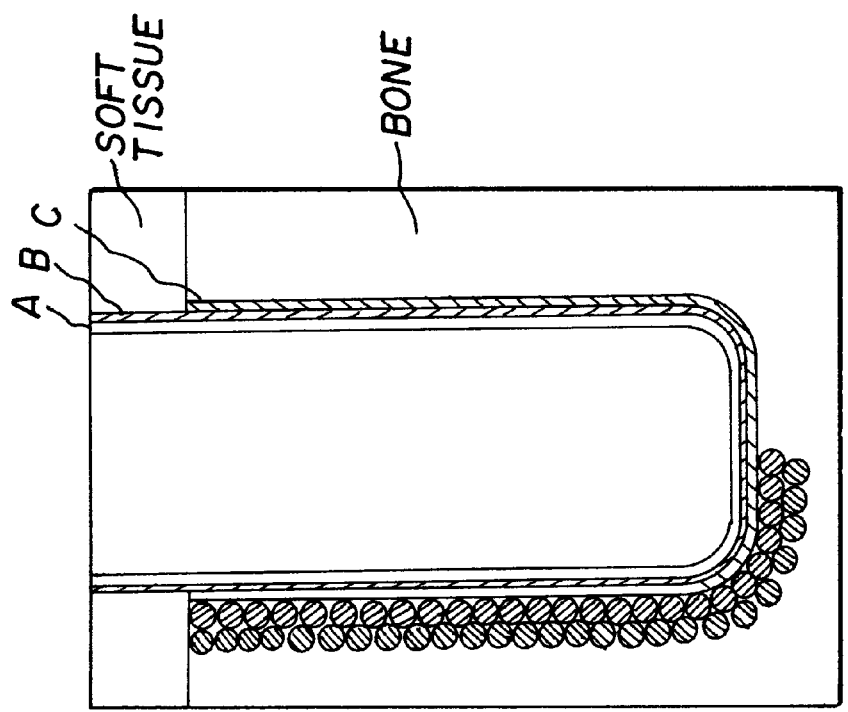
Figure 8:
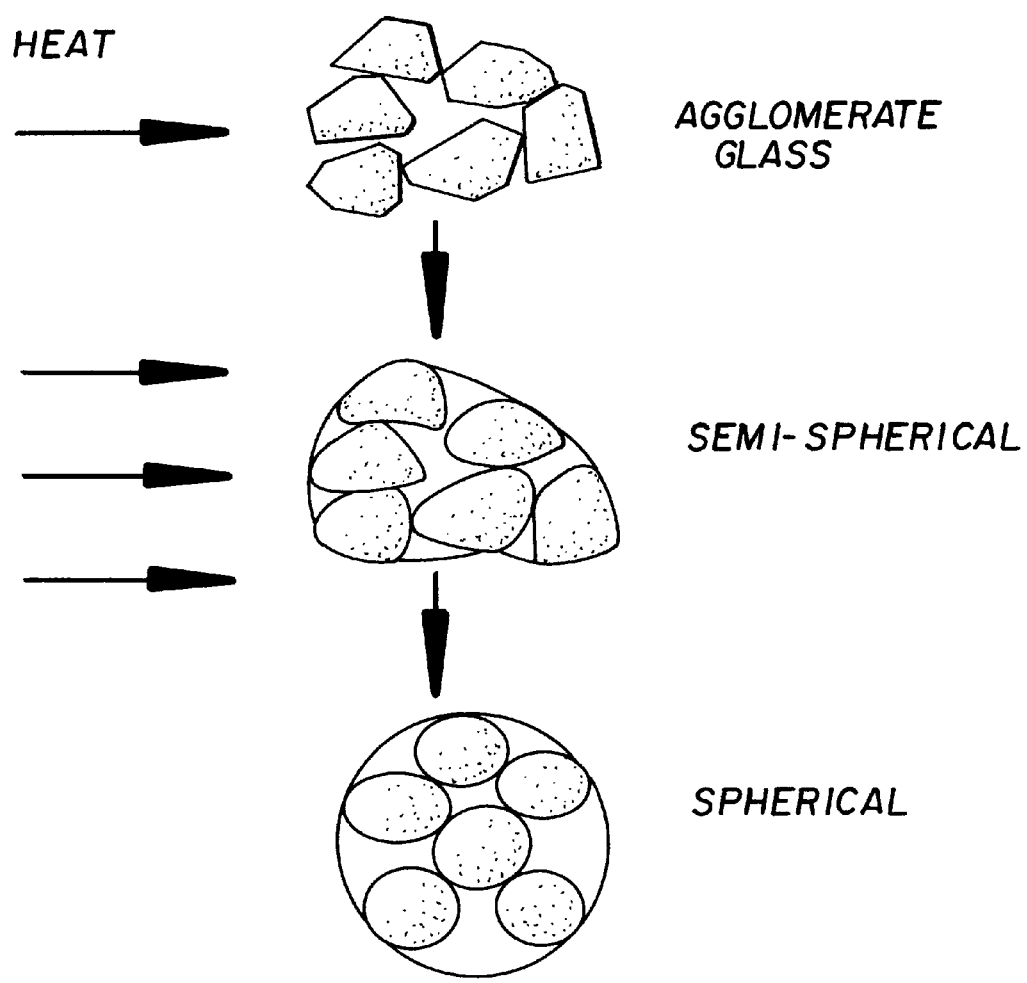
FIG. 8 illustrates the preparation of a matrix of spherical glass granules suitable as carriers for desired agents.
Figure 9:
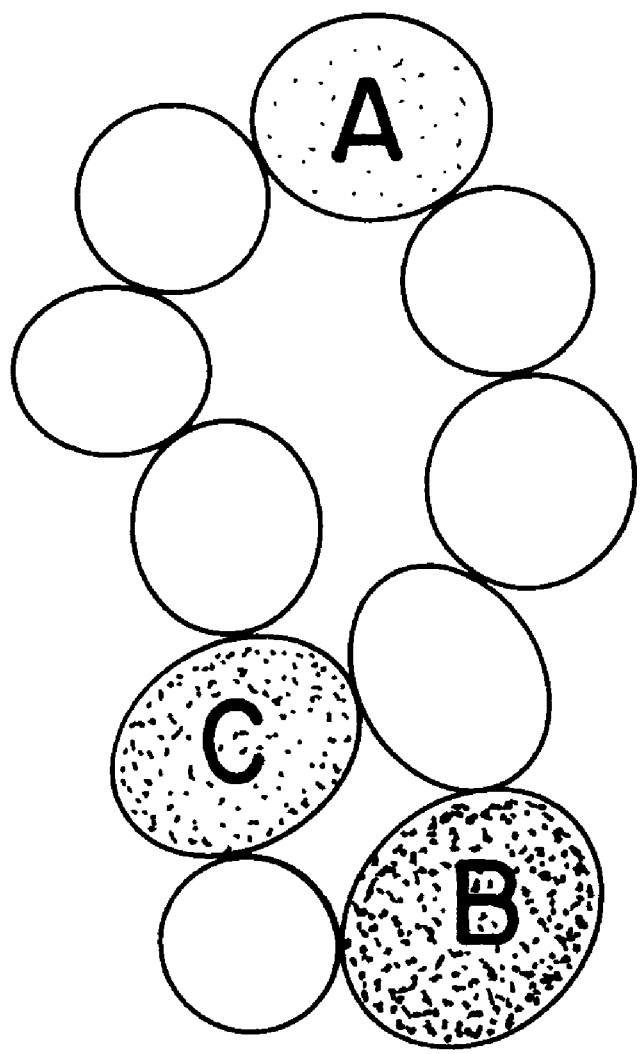
FIG. 9 shows a matrix of different bioactive glass granules (open rings) doped with different agents (A to C).

FIGS. 7a to 9 illustrate some applications of the bioactive glasses according to this invention. FIGS. 7a and 7b illustrate an example of coatings on substrates with a smooth (FIG. 7a) and a rough (FIG. 7b) surface. The first layer A in FIGS. 7a and 7b may be durable and have a thermal expansion coefficient matching that of the substrate. This layer prevents e.g. ion diffusion from the substrate into the surrounding tissues. A possible second layer B may still be fairly durable but nevertheless bond to soft tissue while the third layer C may react with bone. Substrates with one or more coatings may also be used for implantation and, if desired, a layer of spherical bioactive glass granules may be affixed on as an outer layer. FIG. 8 illustrates the use of bioactive glass granules for the preparation of agglomerates. A glass agglomerate made of crushed glass is heated until a semi-spherical shape is obtained. Continued heating results in an agglomerate with spherial granules which may be doped with desired agents, e.g. therapeutically active agents. FIG. 9 shows a matrix of different bioactive glass granules (open rings) doped with different agents A, B and C. This matrix is especially suitable for use in hollow or porous implants designed e.g. for tissue guiding. The different glass granules can be made of bioactive glasses with different durability.

It will be appreciated that the present invention can be incorporated in the form of a variety of embodiments, only a few of which are disclosed herein. It will be apparent for the person skilled in the art that other embodiments exist and do not depart from the spirit of the invention. Thus, the described embodiments are illustrative and should ot be construed as restrictive.

REFERENCES

1. S. A. Barenberg: "Abridged report of the committee to survey the needs and opportunities for the biomaterials industry", J. Biomed. Mater. Res. 22 (1988) 1267–1291.
2. A. Yli-Urpo in "The interface between living tissue and biomaterials", ed. A. Scheinin, Foundation for New Technology, Åbo (1992).
3. K. H. Karlsson and Ö. Andersson in "The interface between living tissue and biomaterials", ed. A. Scheinin, Foundation for New Technology, Åbo (1992).
4. Ö. Andersson: "The bioactivity of silicate glass", Thesis, Åbo Akademi University, Åbo, Finland (1990).
5. Ö. H. Andersson, G. Liu, K. H. Karlsson, L. Niemi, J. Miettinen and J. Juhanoja: "in vivo behaviour of glasses in the $SiO_2$—$Na_2O$—$CaO$—$P_2O_5$—$Al_2O_3$—$B_2O_3$ system", J. Mater. Sci. Mater. Med. 1 (1990) 219–227.
6. M. Karlman: "Bioaktivitet och viskositet hos glas i systemet $Na_2O$—$K_2O$—$MgO$—$CaO$—$B_2O_3$—$P_2O_5$—$SiO_2$", M.Sc. thesis (in Swedish), Åbo Akademi University, Åbo (1992).
7. T. Kokubo, H. Kushitani, S. Sakka, T. Kitsugi and T. Yamamuro: "Solutions able to reproduce in vivo surface-structure changes in bioactive glass-ceramic A-W", J. Biomed. Mater. Res. 24 (1990) 721–734.
8. L. L. Hench in "Handbook of bioactive ceramics", eds. T. Yamamuro, L. L. Hench and J. Wilson, CRC Press, USA (1990).
9. T. Kokubo in "Bone-bonding biomaterials", eds. P. Ducheyne, T. Kokubo and C. A. Blitterswijk, Reed Healthcare Communications, Leiden University, The Netherlands (1992).
10. H. Scholze: "Der Einfluβ von Viskosität und Oberflächenspannung auf erhitzungsmikroskopische Messungen an Gläsern", Ber. Dtsch. Keram. Ges. 39 (1962) 63–68.

We claim:

1. A bioactive glass having a suitable working range for glass processing, said bioactive glass consisting essentially of oxides of silicon, phosphorus, alkali metal, alkaline earths and optionally boron and magnesium wherein said oxides are present in the following amounts:

| | |
|---|---|
| $SiO_2$ | 53–60 wt-% |
| $Na_2O$ | 0–34 wt-% |
| $K_2O$ | 1–20 wt-% |
| MgO | 0–5 wt-% |
| CaO | 5–25 wt-% |
| $B_2O_3$ | 0–4 wt-% |
| $P_2O_5$ | 0.5–6 wt-% | provided that

| | |
|---|---|
| $Na_2O + K_2O =$ | 16–35 wt-% |
| $K_2O + MgO =$ | 5–20 wt-%, and |
| $MgO + CaO =$ | 10–25 wt-%. |

2. The bioactive glass according to claim 1 having the following composition:

| | |
|---|---|
| $SiO_2$ | 53–56 wt-% |
| $Na_2O$ | 10–28 wt-% |
| $K_2O$ | 2–20 wt-% |
| MgO | 0–5 wt-% |
| CaO | 7–25 wt-% |
| $B_2O_3$ | 0–4 wt-% |
| $P_2O_5$ | 0.5–6 wt-% | provided that

| | |
|---|---|
| $Na_2O + K_2O =$ | 18–30 wt-% |
| $K_2O + MgO =$ | 7–20 wt-%, and |
| $MgO + CaO =$ | 12–25 wt-%. |

3. The bioactive glass according to claim 1 wherein $P_2O_5$ is 1–4 wt-% and $B_2O_3$ 1–4 wt-%.

4. A bioactive glass according to claim 1 having a high durability having the following composition:

| | |
|---|---|
| $SiO_2$ | 53–60 wt-% |
| $Na_2O$ | 0–19 wt-% |
| $K_2O$ | 1–17 wt-% |
| MgO | 3–5 wt-% |
| CaO | 5–22 wt-% |
| $B_2O_3$ | 0–4 wt-% |
| $P_2O_5$ | 0.5–6 wt-% | provided that

| | |
|---|---|
| $Na_2O + K_2O =$ | 16–20 wt-% |
| $K_2O + MgO =$ | 5–20 wt-%, and |
| $MgO + CaO =$ | 10–25 wt-%. |

5. The bioactive glass according to claim 4 wherein $SiO_2$ is 54–56 wt-%.

6. A bioactive glass according to claim 1 having a low durability having the following composition:

| | |
|---|---|
| $SiO_2$ | 53–56 wt-% |
| $Na_2O$ | 5–33 wt-% |
| $K_2O$ | 2–20 wt-% |
| MgO | 0–3 wt-% |
| CaO | 7–25 wt-% |
| $B_2O_3$ | 0–2 wt-% |
| $P_2O_5$ | 2–6 wt-% | provided that

| | |
|---|---|
| $Na_2O + K_2O =$ | 25–35 wt-% |
| $K_2O + MgO =$ | 5–20 wt-%, and |
| $MgO + CaO$ | 10–25 wt-%. |

7. The bioactive glass according to claim 1 having the following composition:

| | |
|---|---|
| $SiO_2$ | 54 wt-% |
| $Na_2O$ | 12 wt-% |
| $K_2O$ | 15 wt-% |
| MgO | 5 wt-% |
| $P_2O_5$ | 2 wt-% |

-continued

| | |
|---|---|
| CaO | 11 wt-% |
| B$_2$O$_3$ | 1 wt-%. |

8. The bioactive glass according to claim 1 having the following composition:

| | |
|---|---|
| SiO$_2$ | 53 wt-% |
| Na$_2$O | 6 wt-% |
| K$_2$O | 12 wt-% |
| MgO | 5 wt-% |
| P$_2$O$_5$ | 4 wt-% |
| CaO | 20 wt-%. |

9. The bioactive glass according to claim 2 wherein P$_2$O$_5$ is 1–4 wt-% and B$_2$O$_3$ 1–4 wt-%.

10. A filling material for use in bone defects, in soft tissue, as dental root fillings, or in pulp ectomy, wherein said filling material comprises a bioactive glass according to claim 1, in crushed form or as spherical granules.

11. A material for slow release of agents, wherein said material comprises a bioactive glass according to claim 1, in crushed form or as spherical granules.

12. A dense or porous bulk material for use as filling materials in bone defects, in soft tissue, as dental root fillings, in pulp ectomy, for slow release of agents or for tissue guiding, wherein said material comprises a bioactive glass according to claim 1.

13. A medical or dental implant comprising one or more alloy, metal, glass, ceramic and the like, coated with a coating, wherein said coating comprises a bioactive glass according to claim 1.

14. A material comprising glass fibres or glass wool in the form of single fibres, tissues, fabrics, cords, rings, pressed tablets or pellets and the like for use as filling materials in bone defects, in soft tissue, as dental root fillings, in pulp ectomy, for slow release of agents or for tissue guiding, said material comprising a bioactive glass according to claim 1.

15. An absorbent or adsorbent for phosphorus and/or calcium from a surrounding medium, intended for use in biotechnical processes, said absorbent or adsorbent comprising a bioactive glass according to claim 1.

* * * * *